United States Patent [19]

Bahrmann et al.

[11] Patent Number: 5,808,168
[45] Date of Patent: Sep. 15, 1998

[54] PROCESS FOR THE HYDROFORMYLATION OF OLEFINICALLY UNSATURATED COMPOUNDS

[75] Inventors: Helmut Bahrmann, Hamminkeln; Dieter Frohning, Wesel; Wilhelm Gick, Duisburg; Wolfgang Hofs, Oberhausen; Heinz Kalbfell, Schermbeck; Harald Kappesser, Oberhausen, all of Germany; Peter Lappe, Plano, Tex.; Kurt Schalapski, Oberhausen, Germany; Ernst Wiebus, Oberhausen, Germany; Wolfgang Zgorzelski, Oberhausen, Germany

[73] Assignee: Hoechst Aktiengesellschaft, Germany

[21] Appl. No.: 839,328

[22] Filed: Apr. 17, 1997

[30] Foreign Application Priority Data

Apr. 30, 1996 [DE] Germany .................. 196 17 257.8

[51] Int. Cl.$^6$ .................................................. C07C 45/50
[52] U.S. Cl. ........................................... 568/454; 568/451
[58] Field of Search ...................................... 568/451, 456

[56] References Cited

U.S. PATENT DOCUMENTS 5,367,106 11/1994 Unruh et al. .

FOREIGN PATENT DOCUMENTS

| 0562451 | 9/1993 | European Pat. Off. . |
| 0646563 | 4/1995 | European Pat. Off. . |
| 1337657 | 3/1975 | United Kingdom . |

*Primary Examiner*—Gary Geist
*Assistant Examiner*—Sreeni Padmanabhan
*Attorney, Agent, or Firm*—Bierman, Muserlian and Lucas

[57] ABSTRACT

Waste gas obtained in the hydroformylation of olefinically unsaturated compounds in the presence of an aqueous catalyst solution comprising water-soluble rhodium complexes (1st reaction stage) is fed to a homogeneous reaction system in which residual amounts of the olefinically unsaturated compounds from the first reaction stage are reacted in a homogeneous reaction system (2nd reaction stage).

23 Claims, No Drawings

PROCESS FOR THE HYDROFORMYLATION OF OLEFINICALLY UNSATURATED COMPOUNDS

DESCRIPTION OF THE INVENTION

The invention relates to an improved process for the hydroformylation of olefinically unsaturated compounds in the presence of an aqueous catalyst solution comprising water-soluble rhodium complexes and, in particular, the utilization of the unreacted olefins escaping with the waste gas from the hydroformylation zone.

STATE OF THE ART

The reaction of compounds containing olefinic double bonds with carbon monoxide and hydrogen is the current industrial process for preparing aldehydes (oxo process). The process is not restricted to the use of olefinic hydrocarbons, but also extends to starting materials which have other functional groups in addition to the double bond, primarily functional groups which remain unchanged under the reaction conditions.

The classical oxo process uses cobalt as catalyst whose effectiveness depends on the formation of cobalt carbonyl compounds in the presence of hydrogen and carbon monoxide at pressures above 20 MPa and temperatures of about 120° C. and more over metallic cobalt or cobalt compounds. In the last 30 years, cobalt has increasingly been replaced by rhodium as catalyst. The platinum metal is used as a complex containing, apart from carbon monoxide, preferably phosphines as ligands. Rhodium as catalyst enables the reaction to be carried out at low pressures and also gives higher yields and, when straight-chain terminal olefins are used as starting materials, preferentially forms the unbranched products which are more valuable for further processing.

A further improvement of the oxo process comprises the change from catalysts homogeneously dissolved in the reaction medium, i.e. in the starting material and in the reaction product, to aqueous catalyst solutions which are present as a separate phase from the starting material and reaction product. This variant of the reaction is described, for example, in DE-B-26 27 354 and its particular advantage is easy separation of reaction product and catalyst which is carried out under mild conditions without use of thermal process steps which therefore avoids losses which occur as a result of further reactions of the aldehydes formed. Furthermore, very high yields are obtained and, when using unbranched terminal olefins, n-aldehydes are predominantly obtained.

For reasons of process economics, particularly to avoid large reactors or long reaction times, the reaction is not carried to complete consumption of the olefinically unsaturated compounds, but frequently only until from 60 to 95% of the starting material has been converted into the desired end product. The waste gas leaving the hydroformylation zone therefore comprises not only excess carbon monoxide and hydrogen but also unreacted olefinic starting material. While in the past, these useful materials were frequently not recovered, efforts are nowadays made to utilize them as completely as possible. These efforts have led to the development of a series of processes of different types.

In one known process (cf. EP 0 111 257 B1), waste gas coming from a hydroformylation stage in which olefin is reacted with carbon monoxide and hydrogen at low pressure in the presence of an aqueous catalyst solution comprising rhodium complexes is reacted in a second stage according to the classical oxide process at high pressure and in the presence of cobalt catalysts. This process has been found to be very useful in practice, particularly when it was possible to combine a modern formylation plant with an existing plant using cobalt as catalyst.

In another method of operation (cf. EP 01 88 246 B1), two rhodium-catalyzed hydroformylation stages are connected in series. In the first stage, olefin, carbon monoxide and hydrogen are reacted in the presence of a soluble rhodium-phosphorus complex catalyst, free phosphorus ligands and relatively high-boiling aldehyde condensation by-products with recirculation of liquid or gas. The waste gas comprising olefin, possibly aldehyde, also hydrogen, carbon monoxide and alkane by-product is fed to a decoupled, i.e. operated separately from the first stage, secondary rhodium-catalyzed hydroformylation process in which the waste gas is reacted with added carbon monoxide and hydrogen with recirculation of liquid or gas. This process has the restriction that the hydroformylation in both the first and second stages has to be carried out in the presence of a catalyst homogeneously dissolved in the reaction mixture. The substantial matching of the reaction conditions, particularly the catalyst system in the main and subsequent reaction, virtually rules out the presence in the waste gas from the first stage of components which could adversely affect the hydroformylation in the second stage.

The transfer of the two-stage reaction carried out in homogeneous phases to a process which employs aqueous catalyst solutions in the first and in the second stage is not possible with justifiable technical effort. It fails because the waste gas of the primary stage contains the olefin in a low concentration as a result of the high conversion. Therefore, when using a catalyst system dissolved in water, the processing of the waste gas requires either long reaction times or particular technical measures to restrict the reaction time while nevertheless achieving a high conversion.

OBJECTS OF THE INVENTION

It is an object of the invention to develop a process which allows, under economically justifiable conditions, the conversion of olefinic compounds present in the waste gas of a hydroformylation reaction carried out using an aqueous catalyst solution into carbonyl compounds.

This and other objects and advantages of the invention will become obvious from the following detailed description.

THE INVENTION

The invention provides a process for the hydroformylation of olefinically unsaturated compounds, in which the reaction in a first reaction stage is carried out in a heterogeneous reaction system using an aqueous solution comprising, as catalysts, rhodium compounds containing water-soluble organic phosphorus(III) compounds in complexed form at pressures of from 0.4 to 10 MPa wherein waste gas is formed. In this process, the waste gas from the first reaction stage is fed to a second reaction stage in which the residual amounts of the olefinically unsaturated compounds still present in the waste gas are reacted in a homogeneous reaction system in the presence of rhodium complexes of organic phosphorus(III) compounds as catalysts at pressures of from 15 to 40 MPa.

The process of the invention ensures that the major part of the olefinic compounds not reacted in the first stage and present in the waste gas are hydroformylated in the second stage. In this way, frequently more than 98%, based on the total process, of the starting materials used can be converted into the desired carbonyl compounds, with the conversion essentially depending on the type of starting material and the reaction conditions in the two stages. Worthy of particular emphasis is the fact that by-products which cannot be utilized or are difficult to utilize are formed only in very minor amounts.

The high efficiency of the process of the invention was not foreseeable because, inter alia, the olefinic compounds are considerably diluted in the waste gas. Thus, for example, in the hydroformylation of lower olefins, the proportion of the unreacted olefinic starting material in the waste gas is only from about 20 to 50% by weight. In this type of reaction, such concentrations stand in the way of substantial reaction of the unsaturated starting compound.

The impurities carried from the first reaction stage with the waste gas, which are, inter alia, degradation products of the catalyst system (e.g. mercaptans) and water, the solvent for the catalyst in the first stage, surprisingly do not impair the effectiveness of the catalyst in the second stage. Such behavior was not to be expected because, in particular, organic derivatives of hydrogen sulfide are known to be catalyst poisons. It needs to be taken into account here that mercaptans are hardly soluble in water, as a result of which they do not get into the catalyst solution of the first reaction stage and therefore cannot damage the catalyst either. Instead, the mercaptans accumulate in the homogeneous catalyst-containing reaction mixture of the second stage because of their good solubility in organic media. In addition, water also forms complexes with rhodium and can therefore, at least partially, replace the organic phosphorus ligands in the homogeneously dissolved rhodium complexes to form catalytically inactive substances.

The first reaction stage of the process of the invention is carried out as a heterogeneous reaction in a two-phase system, a reaction which is described, for example, in DE-B-26 27 354. This process is characterized by the presence of an organic phase comprising the olefinic starting material and the reaction product and an aqueous phase in which the catalyst is dissolved. Catalysts used are water-soluble rhodium complexes containing water-soluble organic phosphorus(III) compounds as ligands.

Examples of water-soluble phosphorus(III) compounds which form complexes with rhodium are triarylphosphines, trialkylphosphines and arylated or alkylated diphosphines whose organic radicals contain sulfonic acid groups or carboxyl groups. Their preparation and use is known, for example, from DE-B 26 27 354, EP 0 103 810 B1, EP 0 163 234 B1 and EP 0 571 819 A1. Further groups of suitable compounds are sulfonated or carboxylated organic phosphites and also heterocyclic compounds of trivalent phosphorus (cf. for example EP 0 575 785 A1, EP 0 646 588 A1).

The conditions under which the reaction in the first reaction stage proceeds can be varied within wide limits and can be matched to the individual circumstances. They depend, inter alia, on the starting material, on the catalyst system selected and on the desired degree of conversion. The hydroformylation of the starting materials is usually carried out at temperatures of 50° to 180° C. Preference is given to using temperatures of 80° to 140° C. and particularly 100° to 130°. The total pressure extends over a range of 0.4 to 10 MPa, preferably 1 to 6 MPa and more preferably 1.5 to 5 MPa. The molar ratio of hydrogen to carbon monoxide is usually in a range from 1:10 to 10:1; mixtures comprising hydrogen and carbon monoxide in a ratio of from 3:1 to 1:3 and more preferably about 1:1 are particularly suitable.

The rhodium concentration is from 20 to 1,000 ppm by weight, preferably from 50 to 500 ppm by weight and more preferably from 100 to 300 ppm by weight, in each case based on the aqueous catalyst solution. Although it is possible for the catalyst used to be the stoichiometric rhodium-phosphorus complex, the reaction is usually carried out in the presence of excess phosphorus ligands, i.e. ligand which has not undergone complex formation with rhodium. Preference is given to using 3 to 200 mol of phosphorus in the form of a water-soluble organic phosphorus compound per mol of rhodium. Molar ratios of rhodium to phosphorus in the range from 1:50 to 1:100 have been found to be particularly useful.

The rhodium-phosphorus complex catalyst does not have to have a uniform composition, but can, for example, comprise a mixture of rhodium complexes which have different types of phosphorus ligands. Likewise, the free phosphorus ligand present in the aqueous catalyst solution can be composed of a mixture of different water-soluble organic phosphorus compounds. The catalyst is usually formed in the reaction mixture under the conditions of the hydroformylation reaction from the components rhodium or rhodium compound, organic phosphorus compound and synthesis gas. However, it can also be introduced into the reaction stage in a preformed state, i.e. prepared separately.

In terms of process technology and apparatus too, the first stage of the new process can be varied within wide limits. A useful embodiment of the heterogeneous hydroformylation using an aqueous catalyst phase is described in EP 0 103 810 B1. It has been found to be advantageous to circulate the catalyst solution and to make up for any catalyst losses by feeding in fresh catalyst.

To increase the conversion per unit time of olefinically unsaturated compounds which are only sparingly soluble in the aqueous catalyst solution, it can be advisable to add a phase transfer reagent (solubilizer) to the solution. The phase transfer reagent alters the physical properties of the interfaces between the two liquid phases and aids the transfer of the organic reactants into the aqueous catalyst phase.

Known solubilizers are compounds whose hydrophilic groups are ionic (anionic or cationic) or nonionic. The anionic compounds include sodium, potassium or ammonium salts of carboxylic acids, preferably those having 8 to 20 carbon atoms and more preferably salts of saturated fatty acids having 12 to 18 carbon atoms, also alkylsulfates, alkylbenzene sulfonates and alkylbenzene phosphates. Examples of cationic solubilizers are tetraalkylammonium and N-alkylpyridinium salts.

The nonionic phase transfer reagents do not dissociate into ions in aqueous solution. They include alkylpolyethylene glycols, alkylphenylpolyethylene glycols, fatty acid alkylolamines and trialkylamine oxides. Ampholytes such as aminocarboxylic acids, betaines and sulfobetaine can also be employed as solubilizers. Corresponding processes are described, for example, in EP 0 157 316 B1.

Finally, it is also possible to use rhodium complexes which simultaneously act as catalyst and phase transfer reagent. Such a procedure is, for example, subject matter of EP 0 163 234 B1.

In the first reaction stage, a very substantial conversion of the olefinically unsaturated compounds is usually sought. However, in some cases, the reaction can also be carried out to some degree of partial conversion.

The waste gas (waste gas stream) leaving the first reaction stage is composed of the waste gas taken directly from the reactor (reactor waste gas) to avoid accumulation of inerts in the circulated gas mixtures and the gaseous components arising in the separation of catalyst solution and crude reaction product in the phase separator (product waste gas). The waste gas stream consists essentially of unreacted olefinic compound, carbon monoxide, carbon dioxide, hydrogen and the hydrogenation products of the olefin. This gas mixture is fed, without further intermediate treatment, in particular without purification, but possibly after mixing in hydrogen alone or a mixture of hydrogen and carbon monoxide, as starting material to a second hydroformylation stage.

The second reaction stage is operated independently of the first stage. In the second stage, the residual amounts of the olefinically unsaturated compounds present in the waste gas stream are reacted with carbon monoxide and hydrogen in a homogeneous reaction system. The term "homogeneous reaction system" means a homogeneous solution composed essentially of solvent, catalyst, olefinically unsaturated compound and reaction product.

The catalysts used are rhodium complexes containing organic phosphorus(III) compounds as ligands. Such complexes and their preparation are known (cf. for example U.S. Pat. No. 3,527,809, U.S. Pat. No. 4,148,830, U.S. Pat. No. 4,247,486, and U.S. Pat. No. 4,283,562. They can be used as uniform complexes or as a mixture of different complexes. The rhodium concentration in the reaction medium extends over a range of about 1 to about 1,000 ppm by weight and is preferably from 10 to 700 ppm by weight. In particular, rhodium is employed in concentrations of from 25 to 500 ppm by weight, in each case based on the homogeneous reaction mixture.

As in the first stage, the catalyst employed can be the stoichiometric rhodium complex. However, it has been found to be advantageous to carry out the hydroformylation in the presence of a catalyst system comprising rhodium-phosphorus complex and free, i.e. excess, phosphorus ligand which no longer forms a complex with rhodium. The free phosphorus ligand can be the same as the rhodium complex, but ligands different from this can also be used. The free ligand can be a uniform compound or comprise a mixture of various organo-phosphorus compounds.

Examples of rhodium-phosphorus complexes which can be employed as catalysts are described in U.S. Pat. No. 3,527,809. Preferred ligands in the rhodium complex catalysts include, for example, triarylphosphines such as triphenylphosphine, trialkylphosphines such as tri(n-octyl) phosphine, trilaurylphosphine, tri(cyclohexyl)phosphine, alkylphenylphosphines, cycloalkylphenylphosphines and organic diphosphites. Owing to its ready availability, triphenylphosphine is employed particularly frequently.

The molar ratio of rhodium to phosphorus is usually from 1:1 to 1:300, but the molar proportion of the phosphorus in the form of organic phosphorus compounds can also be higher. Preference is given to using rhodium and organically bound phosphorus in molar ratios of from 1:3 to 1:200. When using triarylphosphines, Rh/P molar ratios of 1:50 to 1:150 have been found to be particularly useful. If trialkylphosphines are used as ligands, the molar ratio of rhodium to phosphorus is preferably from 1:3 to 1:20.

The hydroformylation reaction is carried out in the presence of a solvent. Solvents used are organic compounds in which starting material, reaction product and catalyst system are soluble. Examples of such compounds are aromatic hydrocarbons such as benzene, toluene or the xylenes. Other solvents which can be used are paraffin oil, ketones or ethers.

Solvents which have been found to be particularly useful are the relatively high-boiling condensation compounds of the aldehydes which are formed as by-products in the hydroformylation. The proportion of solvent in the reaction medium can be varied over a wide concentration range and is usually between 20 and 90% by weight, preferably from 50 to 80% by weight, based on the reaction mixture.

The reaction pressure in the second stage of the total process is in the range from 15 to 40 MPa. It has been found to be particularly useful to employ pressures between 15 to 35 MPa, preferably from 20 to 30 MPa. Such ranges are unusual for hydroformylations in homogeneous reaction systems and in the presence of complexes of rhodium and organic phosphorus compounds, regardless of whether the reaction is carried out in one or more stages. The volume ratio of hydrogen to carbon monoxide is from 1:10 to 10:1, preferably from 1:3 to 3:1 and more preferably 1:1.

The reaction temperatures in the second stage of the process of the invention are from 50° to 160° C. Temperatures of from 60° to 150° C. and particularly 75° to 140° C. are preferred.

As already mentioned, the reaction product from the first reaction stage is separated in a phase separator from the aqueous catalyst solution which is returned to the process. According to a useful embodiment, the crude aldehyde is passed through a stripping column countercurrent to fresh synthesis gas. In this way, heat is transferred from the aldehyde to the synthesis gas and the olefinic compound dissolved in the aldehyde is stripped from the crude product and is, together with the heated synthesis gas, again fed to the reaction.

The reaction product of the second reaction stage is distilled off from the catalyst. It can be combined with the product of the first stage and processed further, e.g. distilled. The catalyst-containing distillation residue from the second reaction stage which remains after separating off the aldehyde is, if appropriate, after addition of fresh catalyst and removal of part of the aldehyde condensation products formed during the course of the reaction, recirculated to the reaction zone.

The reaction of straight-chain, terminal olefinically unsaturated compounds in the second reaction stage, i.e. using catalyst homogeneously dissolved in the reaction medium, gives as reaction product an aldehyde mixture containing a higher proportion of iso compound than the product of the first stage, i.e. the reaction using a heterogeneous catalyst phase. The new process therefore makes it possible to match the proportions of n- and iso- compound in the reaction product of the overall process to the actual requirements by selection of the olefin conversion in the first stage. According to a further embodiment of the process of the invention, the ratio of n- and iso- compound in the overall process can also be influenced by addition of olefin to the waste gas mixture which is fed to the second reaction stage. Regardless of the type of olefinically unsaturated starting materials, the formation of relatively high molecular weight, further reaction products of the aldehydes (thick oil) in the secondary stage is very low.

The process of the invention can be applied to olefinically unsaturated compounds of any structure. Accordingly, suitable starting materials are olefins having an internal or terminal double bond and likewise straight-chain or branched olefins. Furthermore, the olefins can also be additionally substituted by functional groups, particularly those which are not changed during the course of the reaction. olefinically unsaturated compounds having a plurality of double bonds are also suitable as starting materials. The process has been found to be particularly useful in the hydroformylation of olefinically unsaturated hydrocarbons having 3 to 6 carbon atoms in the molecule, preferably propylene and the isomeric butenes.

In the following examples, there are described specific embodiments to illustrate the invention. However, it should be understood that the invention is not intended to be limited to the specific embodiments.

EXAMPLE 1

1st Reaction Stage

In a reactor, rhodium acetate and triphenylphosphine trisulfonate sodium salt (TPPTS) were reacted while stirring vigorously at a synthesis gas pressure ($CO:H_2=1:1$) of 5 MPa and a temperature of 122° C. to form the active, water-soluble catalyst $HRhCo(TPPTS)_3$. Rhodium compound and TPPTS were used in such an amount that the rhodium concentration in the aqueous catalyst solution was 300 ppm by weight and the molar ratio of rhodium to phosphorus was about 1:100.

Via a distributor ring at the bottom of the reactor, preheated propylene was fed into the reaction zone and the olefin was reacted there with carbon monoxide and hydrogen at 122° C. and 5 MPa. The product stream comprising gaseous and liquid constituents was removed from the upper part of the reactor and conveyed to a phase separator in which the separation of the aqueous catalyst solution from the crude organic reaction product and from product waste gas took place. The product waste gas was combined with the reactor waste gas to form the waste gas stream. Reactor waste gas was taken from the reactor to avoid accumulation of inert substances in the gas mixture which was circulated. On further cooling, a liquid condensate (waste gas condensate) consisting essentially of propylene and propane separated from the waste gas stream.

The catalyst solution obtained in the phase separator was pumped back into the reactor and the crude aldehyde was passed through a downstream stripping column countercurrent to synthesis gas. In this column, heat was transferred from the aldehyde to the synthesis gas and at the same time, the synthesis gas stream carried out propylene and propane dissolved in the crude aldehyde. As a result of this cooling, water separated from the aldehyde and was returned to the catalyst circuit. Under the reaction conditions selected, the propylene conversion was, depending on throughput and purity of the olefin, between 81 and 91% and the ratio of n-aldehyde to i-aldehyde was about 20:1.

2nd Reaction Stage

Waste gas stream and waste gas condensate from the first reaction stream were, if appropriate, supplemented by hydrogen and/or carbon monoxide and/or propylene and together with the catalyst solution were compressed to 21 MPa and fed to the second reactor. The catalyst comprised relatively high-boiling aldehyde condensation products in which triphenylphosphine (TPP) and the rhodium complex $HRhCo(TPP)_3$ were dissolved. The feed mixture was introduced into the reactor from the bottom at a space velocity of 0.5 v/v·h. It had about the following composition (all figures in % by weight).

| | |
|---|---|
| Hydrogen | 2.20 |
| Carbon monoxide | 29.94 |
| Carbon dioxide | 0.31 |
| Inerts | 1.29 |
| Propylene | 40.01 |
| Propane | 10.19 |
| n-Butyraldehyde | 6.98 |
| Isobutyraldehyde | 0.54 |
| Butanols | 0.77 |
| C8 components | 1.60 |
| >C8 components | 2.76 |
| Triphenylphosphine | 1.21 |
| Triphenylphosphine oxide | 0.50 |
| Water | 1.69 |
| Sulfur | Traces |

The molar ratio of phosphorus to rhodium was about 80:1 and the reactants were reacted at 132° C. 99% of the propylene used (i.e. the unreacted propylene from the first reaction stage and any propylene added to the waste gas stream before it entered the second reactor) were converted into aldehyde. The product stream leaving the second reactor was depressurized via a separator. Apart from a liquid phase, the crude aldehyde product in the gaseous phase, which was depressurization gas, was fractionally condensed to separate off remaining aldehydes.

The crude aldehyde was distilled from the catalyst in a first column and separated into n- and i-butyraldehyde in a second column. The catalyst, which was obtained as a liquid residue in the first column, was mostly returned to the reactor. Only a small substream was bled off in such an amount that the concentration of the relatively high-boiling aldehyde condensation products used as solvent for the rhodium catalyst remained approximately constant in the second reactor. Under the reaction conditions selected, the ratio of n-aldehyde:i-aldehyde was 65:35.

EXAMPLE 2

1st Reaction Stage

In the first reaction stage, the reactants were reacted in the same way as described in Example 1.

2nd Reaction Stage

Waste gas stream and waste gas condensate were, if appropriate, supplemented by hydrogen and/or carbon monoxide and/or propylene and were reacted in an autoclave at a pressure of from 25 to 27 MPa and a temperature of 130° C. Per 1,500 g of propylene, use was made of 80 mg of rhodium and different amounts of trilaurylphosphine so that the molar ratio of rhodium to phosphine was 1:5 or 1:10. The results are shown in the table below and they were compared with the results obtained when using Rh/TPP as catalyst.

TABLE

| | Trilaurylphosphine | | Triphenylphosphine |
|---|---|---|---|
| Rh/P ratio | 1:5 | 1:10 | 1:10 |
| Conversion (%) | 96 | 98 | 95 |
| n/iso ratio | 64/36 | 64/36 | 61/39 |

Various modifications of the process of the invention may be made without departing from the spirit or scope thereof and it is to be understood that the invention is intended to be limited only as defined in the appended claims.

What we claim is:

1. A process for the hydroformylation of olefinically unsaturated compounds comprising reacting in a first reaction stage olefinically unsaturated compounds with hydrogen and carbon monoxide in a heterogeneous reaction system using an aqueous solution comprising, as catalysts, rhodium compound containing water-soluble organic phosphorus(III) compounds in complexed form at pressures of from 0.4 to 10 MPa whereby a waste gas is formed and reacting the waste gas from the first reaction stage in a second reaction stage wherein the residual amounts of the olefinically unsaturated compounds still present in the waste gas with hydrogen and carbon monoxide in a homogeneous reaction system in the presence of rhodium complexes of triaryl phosphines, trialkyl phosphines or organic diphosphites as catalysts at pressures of 15 to 40 MPa.

2. The process of claim 1, wherein the hydroformylation in the first reaction stage is carried out at a temperature of 50° to 180° C. and a rhodium concentration of from 20 to 1,000 ppm by weight, based on the aqueous catalyst solution, and the molar ratio of rhodium to phosphorus in the catalyst solution is from 1:3 to 1:200.

3. The process of claim 1, wherein the pressure in the first reaction stage is 1 to 6 MPa.

4. The process of claim 3, wherein the pressure is 1.5 to 5 MPa.

5. The process of claim 1, wherein the temperature in the first reaction stage is 80° to 140° C.

6. The process of claim 5, wherein the temperature is 100° to 130° C.

7. The process of claim 1, wherein the concentration of the rhodium in the aqueous catalyst solution is from 50 to 500 ppm by weight.

8. The process of claim 7, wherein the concentration is 100 to 300 ppm by weight.

9. The process of claim 1, wherein the molar ratio of rhodium to phosphorus in the aqueous catalyst solution is from 1:50 to 1:100.

10. The process of claim 1, wherein the water-soluble organic phosphorus(III) compounds used are selected from the group consisting of sulfonated or carboxylated aliphatic, aromatic and mixed aliphatic-aromatic phosphines and phosphites.

11. The process of claim 1, wherein the hydroformylation in the second reaction stage is carried out in the presence of a solvent at a temperature of 50° to 160° C. and a rhodium concentration of 1 to 1,000 ppm by weight, based on the homogeneous reaction mixture, and the molar ratio of rhodium to phosphorus in the reaction mixture is 1:1 to 1:300.

12. The process of claim 8, wherein the pressure in the second reaction stage is 15 to 35 MPa.

13. The process of claim 12, wherein the pressure is 20 to 30 MPa.

14. The process of claim 8, wherein the temperature in the second reaction stage is 60° to 150° C.

15. The process of claim 14, wherein the temperature is 75° to 140° C.

16. The process of claim 8, wherein the rhodium concentration in the second reaction stage is 10 to 700 ppm by weight based on the reaction mixture.

17. The process of claim 16, wherein the concentration of rhodium is 25 to 500 ppm by weight based on the reaction mixture.

18. The process of claim 8 wherein, in the second reaction stage, the molar ratio of rhodium to phosphorus in the reaction mixture is 1:3 to 1:200.

19. The process of claim 8, wherein the organic phosphorus(III) compounds used are selected from the group consisting of aliphatic, aromatic and mixed aliphatic-aromatic phosphines and phosphites.

20. The process of claim 19, wherein the organic phosphorus(III) compound used is a triarylphosphine and the molar ratio of rhodium to phosphorus in the reaction mixture is 1:50 to 1:150.

21. The process of claim 20, wherein the triarylphosphine is triphenylphosphine.

22. The process of claim 19, wherein the organic phosphorus(III) compound is a trialkylphosphine and the molar ratio of rhodium to phosphorus in the reaction mixture is 1:3 to 1:20.

23. The process of claim 22, wherein the trialkylphosphine is trilaurylphosphine.

* * * * *